United States Patent [19]
Cliffe et al.

[11] Patent Number: 6,056,942
[45] Date of Patent: May 2, 2000

[54] 5-$HT_{1A}$ LIGANDS

[75] Inventors: Ian Anthony Cliffe; Allan Fletcher, both of Slough; Alan Chapman White, Staines, all of United Kingdom

[73] Assignee: John Wyeth & Brother, Ltd., Maidenhead, United Kingdom

[21] Appl. No.: 08/914,131

[22] Filed: Aug. 18, 1997

Related U.S. Application Data

[63] Continuation of application No. 08/436,408, filed as application No. PCT/GB94/00324, Feb. 17, 1994, abandoned.

[30] Foreign Application Priority Data

Feb. 26, 1993 [GB] United Kingdom ............. 9303968

[51] Int. Cl.$^7$ .................. A61K 21/04; C07D 401/00
[52] U.S. Cl. .............. 424/1.81; 424/1.41; 424/1.45; 544/360
[58] Field of Search ................ 424/1.81, 1.45, 424/1.41, 1.65; 544/358, 359, 360, 392, 403

[56] References Cited

U.S. PATENT DOCUMENTS 4,994,258  2/1991  Burn et al. .................. 424/1.11

FOREIGN PATENT DOCUMENTS

| 2230780 | 10/1990 | United Kingdom | .......... C07F 295/10 |
| 2230781 | 10/1990 | United Kingdom | .......... C07D 295/10 |
| 2248836 | 4/1992 | United Kingdom | .......... C07D 403/06 |
| 2255337 | 11/1992 | United Kingdom | .......... C07D 213/75 |

OTHER PUBLICATIONS

Lever, et al., "Synthesis and In Vivo Characterization of O–(t)–(N–1–[–11]Methyl)–2–Br–LSD," Nucl. Med. Biol., vol.16, No. 7, pp. 697–704, 1989.
Chem. Abst. 106(9): 63908e, (1986).
Chem. Abst. 104(11): 8248r, (1986).
H. Sijbesma, Euro. J. Pharm., vol. 187, No. 2 (1990) 209–223.
Chem. Abst. 114(3): 17928d, (1990).
Chem. Abst. 114(25): 240437p, (1991).
Chem. Abst. 117(11): 103411y, (1992).
D. Julius, Annu. Rev. Neurosci., 1991, 14:335–360.
C. Crouzel et al., Nucl. Med. Biol., vol. 19, No. 8, 857–870 (1992).

*Primary Examiner*—José G. Dees
*Assistant Examiner*—Michael G. Hartley
*Attorney, Agent, or Firm*—Rebecca R. Barrett

[57] ABSTRACT

Selective 5-$HT_{1A}$ antagonists radiolabelled with $^3H$ or $^{11}C$ are radiolabelled ligands useful, for example, in pharmacological screening procedures and in positron emission tomography (PET) studies.

3 Claims, No Drawings

5-HT$_{1A}$ LIGANDS

This is a continuation of application Ser. No. 08/436,408, filed May 24, 1995, now abandoned, which is based on PCT/GB94/00324, filed Feb. 17, 1994.

This invention relates to certain 5-HT$_{1A}$ ligands which are radiolabelled with $^3$H or $^{11}$C.

We have found that certain compounds which are 5-HT$_{1A}$ ligands having specified characteristics can be labelled with with $^3$H or $^{11}$C to give radiolabelled ligands making them particularly useful in, for example, pharmacological screening procedures or in positron emission tomography (PET) studies. The 5-HT$_{1A}$ ligands that are suitable for such radiolabelling are selective 5-HT$_{1A}$ antagonists. By the term "selective 5-HT$_{1A}$ antagonists" are meant compounds which:

(1) are highly potent ligands at the 5-HT$_{1A}$ site having an IC$_{50}$ value of 50 nM or less (as determined by procedure A below).

(2) are at least 25 fold selective in terms of their IC$_{50}$ values for the 5-HT$_{1A}$ site compared with their IC$_{50}$ values for other major monoamine receptor sites in the CNS (as determined by procedure B below).

(3) act as antagonists but not agonists in pharmacological models of 5-HT$_{1A}$ receptor function (as determined by procedure C(a) or C(b) below).

Procedure (A)

The compounds are tested for the 5-HT$_{1A}$ binding properties by measuring their ability to displace [$^3$H]-8-OH-DPAT from the 5-HT$_{1A}$ receptor in rat hippocampal membranes according to the procedure of B. S. Alexander and M. D. Wood, J. Pharm. Pharmacol., 1988 40, 888–891. A compound is regarded as highly potent in this procedure if it has an IC$_{50}$ of 50 nM or less.

Procedure (B)

The affinity of the compounds for D$_2$ receptor sites is determined by the procedure of P. Seeman et al. J. Neurochem. 1984, 43, 221–235.

The affinity of the compound for al sites is determined by the procedure of A. L. Morrow, et al. Mol. Pharmacol. 1986, 29, 321.

The affinity of the compound for 5-HT$_{2A}$ sites is determined by the procedure of R. A. Lyon et al. Mol. Pharmacol., 1987, 31, 194–199. (The 5-HT$_{2A}$ site was previously known as the 5-HT$_2$ site).

A compound is regarded as being 25 fold selective if the IC$_{50}$ value for each of the D$_2$, $\alpha_1$ and 5-HT$_{2A}$ sites as determined above is at least 25 times the IC$_{50}$ value for the 5-HT$_{1A}$ site as determined in Procedure (A). Preferably the compound should be 50 fold selective.

In addition to showing selectivity over the D$_2$, $\alpha_1$ and 5-HT$_{2A}$ sites it is also preferable that the compound is 25 fold selective (preferably 50 fold selective) over one or more of the 5-HT$_{1B}$, 5-HT$_{2C}$, 5-HT$_{1D}$, 5-HT$_3$, $\alpha_2$, $\beta$ and D$_1$ sites. The affinity for these sites is determined by the following procedures.

5-HT$_{1B}$: B. J. Alexander et al., Br. J. Pharmac., 1986, 87, P 22.

5-HT$_{2C}$: B. J. Alexander et al., Br. J. Pharmac., 1986, 87, P 22. (The 5-HT$_{2C}$ site was previously known as the 5-HT$_{1C}$ site).

5-HT$_{1D}$: C. Waeber et al., Naunyn-Schmniedebergs Arch. Pharmacol. 1988, 337, 595–601.

5-HT$_3$: N. M. Barnes et al. J. Pharm. Pharmacol. 1988, 40, 548–551.

$\alpha_2$: D. J. Loftus et al. Life Sciences, 1984, 34, 61–69.

$\beta$: L. T. Williams and R. J. Lefkowitz (1987) Receptor binding studies in adrenergic pharmacology, Raven Press, New York.

D$_1$: V Billard et al. Life Sciences. 1984, 35, 1885–1893.

Procedure (C)

This procedure determines whether a compound that has 5-HT$_{1A}$ binding activity (as determined by procedure (A)) possesses agonist and/or antagonist activity. Brain 5-HT$_{1A}$ receptors exist as two populations in the brain i.e. postsynaptic 5-HT$_{1A}$ receptors and presynaptic somatodendritic 5-HT$_{1A}$ receptors. The presynaptic receptors are particularly sensitive to the agonist properties of 5-HT$_{1A}$ receptor ligands and are activated by compounds designated 'partial agonists'. which function as antagonists at the postsynaptic receptor. "Partial agonists" dose-dependently activate presynaptic receptors but "antagonists" do not display significant agonist activity in models of either postsynaptic or presynaptic 5-HT$_{1A}$ receptor function but act as antagonists in both types of model. The activation of presynaptic 5-HT$_{1A}$ receptors results in the inhibition of serotonin neurones which can be quantified in two ways:

(a) Electrophysiologically monitoring the activity of the neurones to measure their firing rate by the method of H. J. Haigler and G. K. Aghajanian, J. Pharmacol. Exp. Therap., 1974, 188, 688. An intravenous ID$_{50}$ dose is determined. The agonist. 8-OH-DPAT, has an ID$_{50}$ value of 1.9 µg/kg iv. Antagonists are those compounds which meet criteria (1) and (2) above, which do not induce a 50% reduction in neuronal firing rate below a dose of 500 µg/kg iv and which significantly (p<0.05) increase the ID$_{50}$ of the agonist 8-OH-DPAT.

(b) Studying the effect on 5-HT release in the hippocampus using in vivo microdialysis according to the method of C. Routledge, J. Gurling, I. K. Wright and C. T. Dourish, Eur. J. Pharmacol. 239, 195–202. 107, 5P. Agonists and partial agonists significantly reduce 5-HT release following subcutaneous administration, whereas antagonists do not significantly decrease 5-HT release but antagonise the decreased release induced by 8-OH-DPAT.

The present invention provides a selective 5-HT$_{1A}$-antagonist (as hereinbefore defined) radio labelled with $^3$H or $^{11}$C.

Examples of suitable 5-HT$_{1A}$-antagonists which may be radiolabelled are described, for example, in GB-A-2255337, GB-A-2230780, GB-A-2230781 and GB-A-2248836. Particularly preferred compounds are (a) N-(2-(1-(4-(2-methoxyphenyl)piperazinyl))ethyl)-N-(2-pyridinyl)cyclohexanecarboxamide and its pharmaceutically acceptable acid addition salts. The compound has an IC$_{50}$ value of 2.2 nM according to procedure (A). In procedure (B) the percentage inhibition of binding by the compound at 10$^{-6}$M was <50% at the following sites: 5-HT$_{1B}$, 5-HT$_{1C}$, 5-HT$_{1D}$, 5-HT$_{2A}$, $\alpha_2$, $\beta$, D$_1$, and D$_2$ (an inhibition of <50% at 10$^{-6}$M means that the binding affinity is very low). Its binding affinity at $\alpha_1$, sites was 230 nM. In procedure (Ca) the compound does not induce 50% inhibition of firing up to doses of 600 µg/kg iv. It significantly (p<0.05) increases the ID$_{50}$ of 8-OH-DPAT. In procedure (Cb). the compound at 1 mg/kg s.c. did not significantly reduce 5-HT release in the hippocampus, indicating a lack of presynaptic 5-HT$_{1A}$ receptor agonist activity. Pretreatment with compound (a) (at 0.1–1 mg/kg S.C) completely blocked the 8-OH-DPAT-induced decrease in 5-HT release demonstrating that the compound is an antagonist at the somatodendritic 5-HT$_{1A}$ autoreceptor. Compound (a) is termed hereinafter WAY-100635.

(b) N-tert-butyl-3-[4-(2-methoxyphenyl)piperazinyl]-2-phenylpropanamide, its (+)-enantiomer and the pharmaceutically acceptable acid addition salts thereof. In procedure (A) the $IC_{50}$ value for the racemate is 34 nM and that of the (+)-enantiomer is 15.5 nM. In procedure (B) the percentage inhibition of binding by the racemate and its (+)-enantiomer at $10^{-6}$M was as follows:

| Binding Site | % inhibition Racemate | (+)-Compound |
|---|---|---|
| $5-HT_{1B}$ | 27 | 22 |
| $5-HT_{2C}$ | 37 | 50 |
| $5-HT_{2A}$ | 37 | 61 |
| $\alpha_1$ | * | ** |
| $\alpha_2$ | 10 | 11 |
| $\beta$ | 20 | 12 |
| $D_1$ | 20 | 22 |
| $D_2$ | 14 | 20 |

*$IC_{50}$ = 1491 nM
**$IC_{50}$ = 1878 nM

In Procedure (Ca) the racemate and the (+)-enantiomer do not induce 50% inhibition of firing up to doses of respectively 2500 and 600 μg/kg iv. At doses of 500 μg/kg iv these compounds significantly (p<0.05) increase the $ID_{50}$ of 8-OH-DPAT. In procedure (Cb). the racemate and its (+)-enantiomer (both at 10 mg/kg s.c.) had no significant effect on extracellular levels of 5-HT in the hippocampus demonstrating that these compounds are devoid of $5-HT_{1A}$ receptor agonist properties. Pretreatment with the racemate (at 10 mg/kg s.c.) and (+)-compound (b) (at 1–10 mg/kg s.c.) completely blocked the 8-OH-DPAT-induced decrease in 5-HT release demonstrating that these compounds are antagonists at the somatodendritic $5-HT_{1A}$ autoreceptor.

(c) R-[(−)-2,3,4,5,6,7-hexahydro-1-4-[1-[4-(2-methoxyphenyl)piperazinyl]]-2-phenylbutyryl-1H-azepine and the pharmaceutically acceptable acid addition salts thereof. The $IC_{50}$ value in procedure (A) is 0.3 nM. In procedure (B) the percentage inhibition of bindings by the compound at $10^{-6}$ M was <50% at the following sites: $5-HT_{1B}$, $5-HT_{1C}$, β and $D_1$. The percentage inhibition of binding by the compound at $10^{-6}$M was 53% at $\alpha_2$ sites. The $IC_{50}$ values at $5-HT_{1D}$, $5-HT_{2A}$, $\alpha_1$ and $D_2$ sites was 2240 nM. 106 nM, 53 nM and 277 nM respectively.

In procedure (Cb), the compound at 1 mg/kg s.c. had no significant effect on extracellular levels of 5-HT in the hippocampus demonstrating that the compound is devoid of $5-HT_{1A}$ receptor agonist properties. Pretreatment with the compound (1 mg/kg s.c.) completely blocked the 8-OH-DPAT-induced decrease in 5-HT release demonstrating that the compound is an antagonist at the somatodendritic $5-HT_{1A}$ autoreceptor.

Accordingly a preferred embodiment of the invention comprises a compound selected from the group consisting of N-(2-(1-(4-(2-methoxyphenyl)-piperazinyl))ethyl)-N-(2-pyridinyl)cyclohexanecarboxamide, N-tert-butyl-3-[4-(2-methoxyphenyl)-piperazinyl]-2-phenylpropanamide or its (+)-enantiomer and R-[(−)-2,3,4,5,6,7-hexahydro-1-4-[1-[4-(2-methoxyphenyl)-piperazinyl]]2-phenylbutyryl-1H-azepine and the pharmaceutically acceptable acid addition salts thereof, said compound being radiolabelled with $^3H$ or $^{11}C$.

Selective $5-HT_{1A}$-antagonists radiolabelled with $^3H$ are useful as standard ligands for studying $5-HT_{1A}$ binding in pharmacological test procedures. For example they may be used in a similar manner to [$^3H$]-8-OH-DPAT (as described in Procedure A above) in measuring the binding properties of other potential $5-HT_{1A}$ ligands. They have the advantage that they may be used in defining $5-HT_{1A}$ ligands as agonists or antagonists at an early stage of screening i.e. before having to do more time-consuming functional studies.

[$^3H$]WAY-100635 has been found to interact with a single class of recognition sites in rat hippocampal membranes. The ligand saturation equilibrium dissociation constant was 0.40±0.05 nM and the kinetically derived value was 0.33 nM. [$^3H$]WAY-100635 binding was reversible and the data support first order dissociation kinetics. The pharmacological binding profile of [$^3H$]WAY-100635 was consistent with recognition of the $5-HT_{1A}$ binding site. WAY-100635 showed the highest potency ($IC_{50}$=3 nM) in inhibiting the binding of [$^3H$]WAY-100635. The $5-HT_{1A}$ antagonist. SDZ-216525. also displayed high potency ($IC_{50}$=5 nM) at hippocampal [$^3H$]WAY-100635 binding sites. NAN 190, 5-CT, 5-HT, 8-OH-DPAT, BMY7378, methiothepin and RU24969 were intermediate in potency ($IC_{50}$=10–100 nM) and PAPP, spiperone, ipsapirone, buspirone, gepirone and ritanserin displayed even weaker inhibition potencies ($IC_{50}$=100 nM–10 μM). Cyanopindolol, (−)propranolol, rauwolscine, yohimbine and clonidine displayed comparatively low potencies ($IC_{50}$=100 nM–100 μM) against [$^3H$]WAY-100635. The 5-HT uptake bloker, fluvoxarnine, was inactive at micromolar concentrations against [$^3H$]WAY-100635 binding. Furthermore, noradrenaline, L-phenylephrine, isoprenaline, dopamine and atropine, all at a concentration of 10 MM, were ineffective at displacing hippocampal [$^3H$]WAY-100635 binding, as were clonazepam and imipramine.

Correlation plots of drug potencies ($IC_{50}$ values) for the inhibition of [$^3H$]WAY-100635 bindings to the human $5-HT_{1A}$ receptor (stably transfected into the Chinese Hamster Ovary cell line) and the rat hippocampal $5-HT_{1A}$ receptor produced correlation coefficient values close to unity (r=0.96: P<0.001, DF=12), revealing a significant agreement between the pharmacological profiles of both human and rodent $5-HT_{1A}$ binding sites.

Radioreceptor autoradiographic studies using rat brain sections demonstrated that the regional distribution of [$^3H$] WAY-100635 parallelled that of the high-affinity binding component of [$^3H$]8-OH-DPAT. a selective $5-HT_{1A}$ agonist. [$^3H$]WAY-100635 labels both agonist high- and low-affinity components of the $5-HT_{1A}$ receptor with equal affinity. [$^3H$]WAY-100635 can be used as a tool to label multiple affinity states of the $5-HT_{1A}$ receptor and to characterise agonist-mediated receptor-effector coupling mechanisms.

Selective 5-HT IA antagonists radiolabelled with $^{11}C$ are useful as radioligands in Positron Emission Tomography (PET) studies. Such studies are carried out in vivo in animals and more preferably in humans. The $^{11}C$ serves as a positron source producing gamma rays. These rays are detected by the PET scanner and the resulting data is processed by computer so as to give information on the distribution of the radioligand in the living subject. There have been previous suggestions for studying the 5-HT system with PET by using radioligands for the various pre- and post-synaptic 5-HT receptors and binding sites. However previously no suitable radioligands have been available for the $5-HT_{1A}$ site.

The $^{11}C$ radiolabelled selective $5-HT_{1A}$ antagonist may be used in the PET studies as for example, a research tool or as a diagnostic aid. For example, the potency and duration of an orally or parenterally administered unlabelled drug, which is a 5-5 $HT_{1A}$ ligand, can be measured by following the displacement of the $^{11}C$ labelled selective $5-HT_{1A}$-antagonist from the brain of humans. Furthermore PET studies using $^{11}C$ radiolabelled selective $5-HT_{1A}$ ligands can be used to study the distribution and nature of $5-HT_{1A}$ receptor sites as a function of disease states (e.g. Alzheimer's Disease or depression) and hence can be used to diagnose such disease states.

The $^3$H and $^{11}$C radiolabelled selective 5-HT$_{1A}$ antagonists may be prepared by methods known in the art. For example a precursor of the antagonist may be reacted with a $^3$H or $^{11}$C containing reagent such that the radioisotope is incorporated into the resulting molecule of the antagonist. For example an ethylenically unsaturated precursor may be catalytically hydrogenated with tritium to provide the $^3$H-radiolabelled selective 5-HT$_{1A}$ antagonist. In a further example a phenol precursor of an antagonist may be alkylated with a radiolabelled alkylating agent, e.g. [$^3$H]methyl iodide or [$^{11}$C]methyl iodide to provide the antagonist containing a radiolabelled methoxy substituted phenyl group. The [$^{11}$C]methyl iodide may be produced via [$^{11}$C] methanol from cyclotron-produced [$^{11}$C]carbon dioxide. The particularly preferred compounds (a), (b) and (c) mentioned above all contain a methoxyphenyl group and hence the radiolabelled compounds may be prepared from the phenol precursors. For example N-(2-(4-(2-hydroxyphenyl)-1-piperazinyl))ethyl)-N-(2-pyridyl)cyclohexane carboxamide may be alkylated with [$^3$H]- or [$^{11}$C]-methyliodide to give $^3$H or $^{11}$C labelled N-(2-(1-(4-(2-methoxyphenyl))-piperazinyl)ethyl)-N-(2-pyridinyl) cyclohexanecarboxamide.

The following Examples illustrate the invention.

EXAMPLE 1

[Methoxy-$^3$H] N-(2-(1-(4-(2-methoxyphenyl) piperazinyl))-ethyl)-N-(2-pyridinyl) cyclohexanecarboxamide Sodium hydride (3 mg) was added to a solution of N-(2-(1-(4(2-hydroxyphenyl)piperazinyl))ethyl)-N-(2-pyridinyl)cyclohexanecarboxamide (8 mg) in DMF (1.5 ml) and the solution stirred at room temperature under nitrogen for 2 hours. [$^3$H]Methyl iodide (1 Ci) was distilled into the reaction mixture which was stirred at room temperature for 1.5 hours. The reaction mixture was then pumped to dryness on the manifold and taken to dryness several times with ethanol. The yield of crude material was 480 mCi.

The crude material was purified by preparative TLC (ethyl acetate:ethanol:triethylamine=100:12.5:0.5) on silica plates. The final yield of product was 132 mCi, at a specific activity of 71 Ci/mmol.

EXAMPLE 2

[Methoxy-$^{11}$C] N-(2-(1-(4-(2-methoxyphenyl)-piperazinyl))-ethyl)-N-(2-pyridinyl) cyclohexanecarboxamide In a suitable manifold, sodium hydride (3 mg) was added to a solution of N-(2-(1-(4-(2-hydroxyphenyl)-piperazinyl)) ethyl)-N-(2-pyridinyl)cyclohexane-carboxamide (8 mg) in dimethyl formamide (1.5 ml) under nitrogen. [$^{11}$C]-Methyl iodide was distilled into the reaction mixture and the reaction heated to 80° C. for 5 min. After purification by HPLC (Beckman Ultrasphere 5μ ODS (25×46 cm) 0.02M potassium dihydrogen orthophosphate:acetonitrile) the material was formulated for iv injection by dissolution in normal saline and sterile millipore filtration.

What is claimed is:

1. A selective 5-HT1A antagonist radiolabeled with 11C wherein the selective 5-HT1A antagonist is N-(2-(1-(4-(2-methoxyphenyl)piperazinyl))ethyl)-N-(2-pyridinyl)-cyclohexanecarboxamide, or a pharmaceutically acceptable salt thereof.

2. [Methoxy-11C] N-(2-(1-(4-(2-methoxyphenyl)-piperazinyl))ethyl)-N-(2-pyridinyl)cyclohexane-carboxamide or a pharmaceutically acceptable salt thereof.

3. A method of imaging a subject by positron emission tomography comprising administering [Methoxy-11C]-N-2-(1-(4-(2-methoxy)-piperazinyl)-ethyl)-N-(2-pyridinyl) cyclohexane-carboxamide, or a pharmaceutical salt thereof to said subject and performing a scan to obtain an image.

* * * * *